United States Patent [19]
Blumberg et al.

[11] Patent Number: 6,060,505
[45] Date of Patent: May 9, 2000

[54] METHOD OF TREATING CANCER USING C-26 MODIFIED BRYOSTATIN

[75] Inventors: Peter M. Blumberg, Frederick; Zoltan Szallasi, Bethesda, both of Md.; George R. Pettit, Paradise Valley, Ariz.

[73] Assignees: The United States of America as represented by the Department of Health and Human Services, Washington, D.C.; Arizona Board of Regents of Arizona State University, Tempe, Ariz.

[21] Appl. No.: 09/142,945

[22] PCT Filed: Mar. 20, 1997

[86] PCT No.: PCT/US97/04515

§ 371 Date: Feb. 16, 1999

§ 102(e) Date: Feb. 16, 1999

[87] PCT Pub. No.: WO97/34598

PCT Pub. Date: Sep. 25, 1997

Related U.S. Application Data

[60] Provisional application No. 60/013,740, Mar. 20, 1996.

[51] Int. Cl.[7] .................................................... A01N 43/02
[52] U.S. Cl. ........................ 514/449; 549/267; 514/451; 514/459; 514/460; 514/883; 514/885; 514/908; 514/950
[58] Field of Search ............................ 549/267; 514/449, 514/451, 459, 460, 883, 885, 908, 950

[56] References Cited

U.S. PATENT DOCUMENTS

| | | | |
|---|---|---|---|
| 4,560,774 | 12/1985 | Pettit et al. | 549/267 |
| 4,611,066 | 9/1986 | Pettit et al. | 549/267 |
| 4,833,257 | 5/1989 | Pettit et al. | 549/267 |

FOREIGN PATENT DOCUMENTS

| | | |
|---|---|---|
| 0 109 811 | 5/1984 | European Pat. Off. . |
| WO 89/05346 | 6/1989 | WIPO . |

OTHER PUBLICATIONS

Al–Katib et al., *Hemotol. Oncol.*,8, 81–89 (1990).
Blumberg et al., *New Leads and Targets in Drug Research*, 33, 273–285 (1992).
Dell' Aquilla et al., *Cancer Research*,47, 6006–6009 (1987).
Dell'Aquilla et al., *Cancer Research*,48, 3702–3708 (1988).
Drexler et al., *Blood*,74, 1747–1757 (1989).
Hergenhahn et al., *Journal of Cancer Research for Clinical Oncology*,104, 31–39 (1982).
Kazanietz et al., *Molecular Pharmacology*,46, 374–379 (1994).
Kazanietz et al., *Molecular Pharmacology*,44, 298–307 (1993).
Kraft et al., *Proc. Natl. Acad. Sci. USA*,83, 1334–1338 (1986).
Kraft, A., *Journal of the National Cancer Institute*,85 (22), 1790–1791 (1993).
Lewin et al., *Cancer Communication*,3 3, 67–70 (1991).
Lewin et al., *Biochemical Pharmacology*,43 (9), 2007–2014 (1992).
Lily et al., *Cancer Research*,50, 5520–5525 (1990).
Mackanos et al., *The Journal of Biological Chemistry*,266 (17), 11205–11212 (1991).
May et al, *Proc. Natl. Acad. Sci. USA*84, 8483–8487 (1987).
Pettit et al., *Journal of American Chemical Society*,104, 6846–6848 (1982).
Pettit et al., *Anticancer Drug Design*,7, 101–113 (1992).
Pettit, G., *Progress in the Chemistry of Organic Natural Products 57*, Springer–Verlag: 1991.
Philip et al., *Journal of the National Cancer Institute*,85 22, 1812–1818 (1993).
Prendiville et al., *Br. J. Cancer*,68, 418–424 (1993).
Rando et al., *Biochemistry*,31, 2211–2218 (1992).
Schucter et al., *Cancer Research*,51, 682–687 (1992).
Sredni et al., *Immunology*,70, 473–477 (1990).
Szallasi et al., *Molecular Pharmacology*,46, 840–850 (1994).
Szallasi et al., *The Journal of Biological Chemistry*,269 (3), 2118–2124 (1994).
Szallasi et al., *Cancer Research*,56, 2105–2111 (1996).
Trenn et al., *Journal of Immunology*,140, 433–439 (1988).
Wender et al., *Proc. Natl. Acad. Sci. USA*,85, 7197–7201 (1988).
Zayed et al., *Planta Med.*,34, 65–69 (1984).
Zhang et al., *Cell*,81, 917–924 (1995).

*Primary Examiner*—Frederick Krass
*Attorney, Agent, or Firm*—Leydig, Voit & Mayer, Ltd.

[57] ABSTRACT

Disclosed are modified bryostatins and their use as anticancer drugs.

40 Claims, 2 Drawing Sheets

METHOD OF TREATING CANCER USING C-26 MODIFIED BRYOSTATIN

Priority is claimed under 35 USC § 119(e) from Provisional application 60/013,740, filed Mar. 20, 1996. Also, this is a 371 of PCT/US97/04515, filed on Mar. 20, 1997.

TECHNICAL FIELD OF THE INVENTION

The present invention relates to modified bryostatins and the use of these compounds as anticancer drugs.

BACKGROUND OF THE INVENTION

Bryostatin is a potential cancer chemotherapeutic agent in clinical trials with positive responses observed for some cancers. Bryostatins are typically isolated from the marine bryozoan *Bugula neritina,* although those skilled in the art will appreciate that other sources for bryostatins and closely related compounds will exist.

Figure 1:
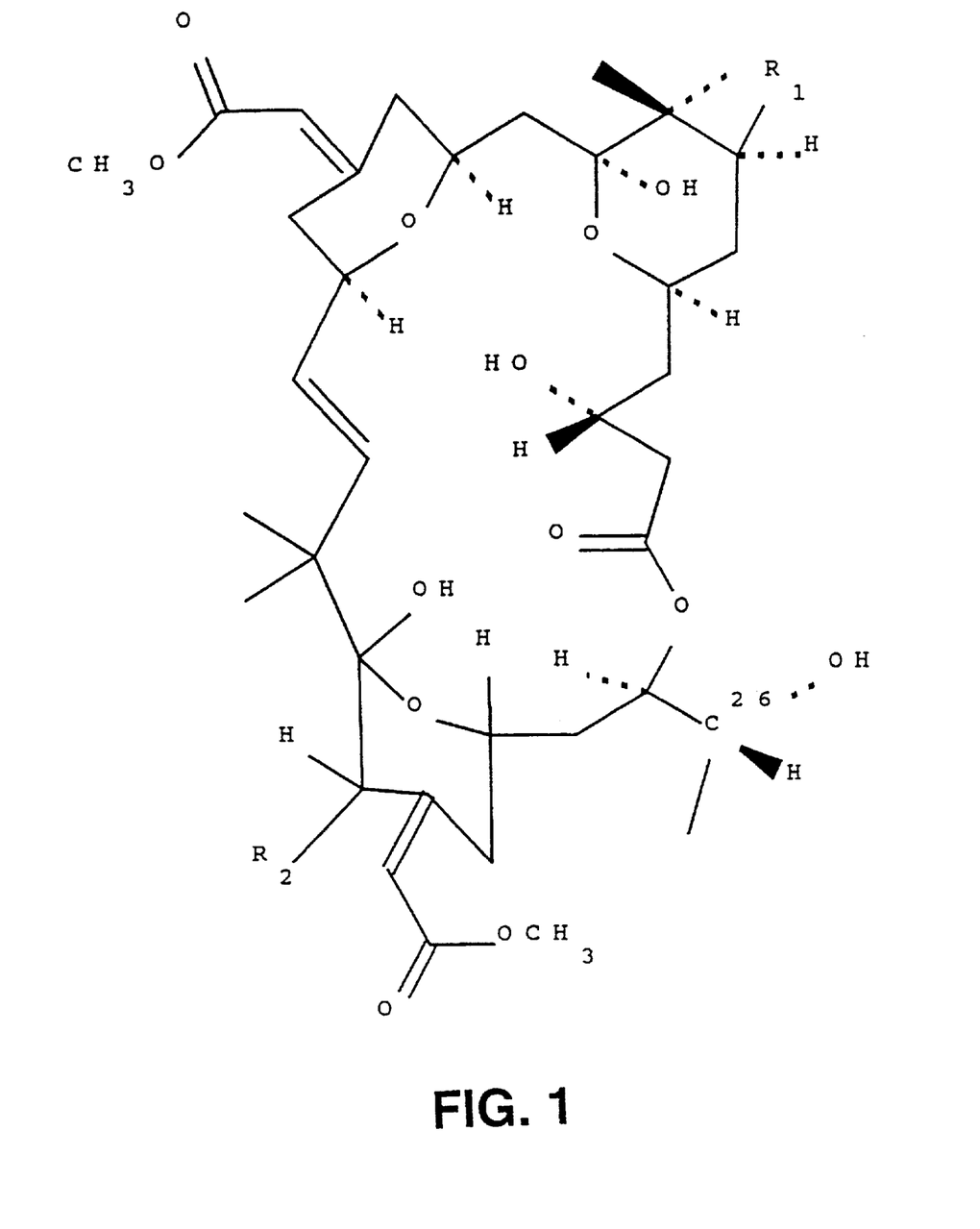
FIG. 1 is a stereochemical rendering of the macrocyclic lactone structure shared by all bryostatins except for bryostatin 3, as determined by the best available method in the art. In the event that an improved method of determining the macrocyclic lactone structure becomes available and such method proves that the macrocyclic lactone structure is, in fact, different, it is the actual such macrocyclic lactone structure which is to be used in characterizing the present invention rather than that depicted in this figure.

Bryostatins comprise macrocyclic lactones of the structure shown in FIG. 1. Bryostatins derived from nature contain $R_1$, and $R_2$ groups selected according to Table 1.

Table 1

Side-chain group designations for isolated bryostatins.

Bryostatins, as a class of compounds, are known to be potent ligands for protein kinase C that function as partial antagonists (Lewin et al., *Biochem. Pharmacol.*, 43, 2007–2014 (1992); Kraft et al., *Proc. Natl. Acad. Sci. USA,* 83, 1334–1338 (1986)). Because of the high affinity of bryostatins for protein kinase C and the central role of protein kinase C activity in the regulation of cellular function, bryostatins have been thought to exert an antineoplastic activity through protein kinase C.

In vitro, bryostatins activate individual protein kinase C isozymes to an extent similar to that of typical phorbol esters (Kazanietz et al., *Mol. Pharmacol.*, 46, 374–379 (1994)). Biologically, however, bryostatins function as a partial antagonist for a subset of phorbol ester induced responses (Blumberg et al., in *New Leads and Targets in Drug Research,* Alfred Benzon Symposium 33, pp. 273–285 (Munksgaard, Copenhagen)). Multiple mechanistic differences have been proposed to contribute to their unique spectrum of biological response, including in vivo selectivity for the protein kinase C isozymes δ and ε (Szallasi et al., *Mol. Pharmacol.*, 46, 840–850 (1994)); slow kinetics of protein kinase C translocation, and protection of protein kinase C-δ from down regulation at high doses (Szallasi et al., *Mol. Pharmacol.*, 46, 840–850 (1994), Szallasi et al., *J. Biol. Chem.*, 269, 2118–2124 (1994)). However, both the protection of protein kinase C-δ (Szallasi et al., supra *J. Biol. Chem.*, (1994)), and the antagonism of phorbol ester action on Friend erythroleukemia cell differentiation (Dell'Aquilla et al., *Cancer Res.,* 47, 6006–6009 (1987)) were demonstrated to be noncompetitive between bryostatin and phorbol ester. These two anomalies demonstrated that the working understanding of bryostatin mechanisms of action was incomplete. One possible explanation would be that bryostatins bind to receptors that phorbol esters do not bind in order to induce their antineoplastic effect. This explanation, if correct, would suggest that the antineoplastic target of bryostatins might not be protein kinase C. Similarly, results comparing the extent of arachidonic acid release induced in C3H10T1/2 cells by bryostatin analogs and phorbol esters suggested similar concepts (Dell'Aquilla et al., *Cancer Res.,* 48, 3702–3708 (1988)). Nonetheless, the antineoplastic actions of bryostatin were still commonly thought to be mediated via the protein kinase C pathway because of a lack of affirmative data to the contrary.

A fairly detailed understanding of both phorbol ester and bryostatin interactions with the phorbol ester binding domain of protein kinase C exists. The structure-activity relationships for the phorbol esters have been extensively examined both for protein kinase C binding (Kazanietz et al., *Mol. Pharmacol.*, 44, 298–307 (1993)) and for biological responses (Hergenhahn et al., *J. Cancer Res. Clin. Oncol.*, 104, 31–39 (1982); Furstenberger et al., *Planta Med.*, 22, 241–266 (1972); Zayed, et al., *Planta Med.*, 34, 65–69 (1984)). The current understanding of the phorbol ester pharmacophore has been further extended both by X-ray crystallography of the complex between phorbol ester and the phorbol ester binding domain of protein kinase C (Zhang et al., *Cell*, 81, 917–924 (1995)), and by computer modeling using the NMR-defined structure of the phorbol ester binding domain in protein kinase C. These approaches uniformly emphasize the central role of the C-20 hydroxyl group of the phorbol ester for the binding interaction. Computer comparison of bryostatin with the phorbol esters indicates that the C-26 hydroxyl group of bryostatin corresponds to the C-20 hydroxyl group of the phorbol ester (Rando et al., *Biochemistry*, 31, 2211–2218 (1992); Wender et al., *Proc. Nat'l. Acad. Sci. USA*, 85, 7197–7201 (1988)). This assignment is supported by the decreased binding activity for protein kinase C of either the C-26 acetate ester of bryostatin (Wender et al., supra (1988)) or of the C-26 epimer of bryostatin 4 (Lewin et al., *Cancer Commun.*, 3, 67–70 (1991)). This decreased binding activity suggested to those skilled in the art that C-26 modified bryostatins would be ineffective as antineoplastic drugs.

As is the case with many drugs, a tension exists between the beneficial activity of the drug and its side-effects. The relationship between the desired action of a drug (e.g., antineoplastic activity) and undesired side-effects (e.g., general toxicity) can be expressed as a "therapeutic index." For instance, a drug with very low general toxicity and average efficacy could be administered at significantly greater dosages than a drug with relatively high general toxicity and only slightly elevated efficacy. The permissibility of higher dosing regimens for the lower toxicity drug and the concomitant increase in total efficacy is expressed by the higher therapeutic index for the lower toxicity drug. As with most chemotherapeutic agents, the maximal dose of bryostatin is limited by toxicity. In mice, bryostatin doses greater than 200 $\mu$g/kg are lethal (Schuchter et al. *Cancer Res.* 51, 682–687 (1992)), whereas in humans three bryostatin infusions of 2 $\mu$g/kg caused significant side-effects including myalgia and hypotension (Prendiville et al., *Br. J. Cancer*, 68, 418–424 (1993); see also, Philip et al., *J. Natl. Cancer Inst.*, 85, 1812–1818 (1993)).

Thus, there exists a need for compounds with the antineoplastic activity of bryostatin for use in the treatment of cancer, but having diminished toxicity. The present invention provides such compounds and methods of using such compounds, particularly in the treatment of cancer. These and other objects of the present invention, as well as additional inventive features, will be apparent from the description of the invention provided herein.

SUMMARY OF THE INVENTION

The present invention provides a method of treating cancer in an animal comprising administering to an animal afflicted with cancer a therapeutically effective amount of a bryostatin which has been modified at the C-26 position as defined herein.

DESCRIPTION OF THE PREFERRED EMBODIMENTS

C-26 modified bryostatin derivatives (including the C-26 stereoisomers of bryostatins, known as 26-epibryostatins, in which the natural configuration of C-26 is changed from R to S) lack high affinity for protein kinase C isozymes (see, for example, Lewin et al., supra (1991)). Thus, they have been generally assumed to lack utility as antineoplastic drugs. Surprisingly, C-26 modified bryostatins, as defined herein, have been found to possess antineoplastic activity equivalent to unmodified bryostatins. While not intending to be bound by any particular theory, it is believed that this phenomenon is possible because protein kinase C is not, in fact, the antineoplastic target of bryostatins, as currently assumed in the field. The modification of bryostatins in the C-26 position has been determined to result in a decreased affinity for protein kinase C and cause a concomitant decrease in general toxicity.

Regardless of the exact etiologies of the antineoplastic effect and the diminished toxicity of C-26 modified bryostatins, a useful correlation between the affinity of bryostatins for protein kinase C and toxicity has now been established. Therefore, a decreased affinity for protein kinase C is a strong indication of reduced toxicity for bryostatins and can be used to estimate therapeutic indices in vitro. These C-26 modified bryostatins used in accordance with the method of the present invention have been determined to be similarly potent for inhibition of cancer cell growth, when compared to unmodified bryostatins, but have about at least a ten-fold reduction in toxicity compared to unmodified bryostatin 1.

The present invention provides a method of treating cancer in an animal comprising administering to an animal afflicted with cancer a therapeutically effective amount of a bryostatin which has been modified at the C-26 position. There appears to be a large degree of flexibility in the precise structures of $R_1$ and $R_2$ which maintain the in vitro biological activity of the bryostatins (Dell'Aquilla et al., *Cancer Res.*, 48, 3702–3708 (1988)). It is thus believed that the desired therapeutic effect of the method of the present invention could be provided if the core structure of the macrocyclic lactone (i.e., the bryostatin structure in the absence of precise $R_1$ and $R_2$ designations) is retained. Consequently, for the purpose of describing the present invention, the term "bryostatin" should be understood to include the macrocyclic lactone structure of bryostatin 1, which is believed to have the structure shown in FIG. 1, wherein $R_1$ and $R_2$ can be independently selected from the group consisting of hydrogen and an organic substituent of from 1 to 20 carbon atoms. Advantageously, $R_1$ and $R_2$ are selected from the group consisting of the substituent groups (i.e. side chains) that naturally occupy these positions (i.e., any structure from Table 1), and preferably $R_1$ and $R_2$ are those which exist together in any one bryostatin derived from nature. Most preferably, $R_1$ and $R_2$ are selected as those naturally existing in bryostatin 1.

One skilled in the art will appreciate that since both $R_1$ and $R_2$ exist in nature as hydrogen, hydroxyl, small esters and larger (e.g., $C_8$) esters, that substantial variations can be reasonably expected to yield antineoplastic bryostatins. In particular, it is advantageous that at least some, preferably, much of the hydrophobic nature of these acyl side chains is preserved. However, the selection of relatively small hydrophilic groups (e.g., hydroxyl) for $R_1$ and $R_2$ does not result in an excessive loss of the hydrophobic character of the $R_1$ and $R_2$ groups since these hydrophilic groups will be found in the overwhelming hydrophobic context of the bryostatin (macrocyclic lactone) core structure. Such a variation is further supported by the existence of experimental evidence indicating that bryostatins lacking either carbonaceous $R_1$ or carbonaceous $R_2$ side chain groups function similarly to bryostatin 1 in vitro (Dell'Aquilla et al., supra (1988). Suitable $R_1$ and $R_2$ substituents can be obtained by reaction with the free hydroxyl groups and replaceable acyl groups of the bryostatins. Thus, various acyl esters of these compounds can be prepared by methods well known to those skilled in the art. Acyl derivatives of the bryostatins include:

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like;

(b) saturated or unsaturated, alicyclic carboxylic acids, for example, cyclobutanecarboxylic acid, cyclopentanecarboxy acid, cyclopentenecarboxylic acid, methylcyclopentanecarboxylic acid, cyclohexanecarboxylic acid, dimethylcyclohexanecarboxylic acid, dipropylcyclohexanecarboxylic acid, and the like;

(c) saturated or unsaturated, alicyclic aliphatic carboxylic acids, for example, cyclopentaneacetic acid, cyclopentanepropionic acid, cyclohexaneacetic acid, cyclophexanebutyric acid, methylcyclohexaneacetic acid, and the like;

(d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropionic acid and naphthylacetic acid, and the like. Suitable halo-, nitro-, hydroxy-, keto-, amino-, cyano-, thiocyano- and lower alkoxyhydrocarbon carboxylic acids include hydrocarboncarboxylic acids as given above which are substituted by one or more of halogen, nitro, hydroxy, keto, amino, cyano, or thiocyano, or loweralkoxy, advantageously lower alkoxy of not more than six carbon atoms, for example, methoxy, ethoxy, propoxy, butoxy, amyloxy, hexyloxy, and isomeric forms thereof. Examples of substituted hydrocarbon carboxylic acids are: mono-, di-, and trichloracetic acid; α- and β-chloropropionic acid; α- and γ-bromobutyric acid; α- and δ-iodovaleric acid; mevalonic acid; 2-and 4-chlorocyclohexanecarboxylic acid; shikimic acid; 2-nitro-1-methyl-cyclobutanecarboxylic acid; 1,2,3,4, 5,6-hexachlorocyclohexanecarboxylic acid; 3-bromo-2-methylcyclohexanecarboxylic acid; 5- and 6-bromo-2-methylcyclohexanecarboxcylic acid; 3-bromo-3-methylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 3,2-dibromo-4-methylcyclohexanecarboxylic acid; 3-bromo-2,2,3-trimethylcyclopentanecarboxylic acid; 1-bromo-3,5-dimethylcyclohexanecarboxylic acid; homogentistic acid, o-, m-, and p-chlorobenzoic acid; anisic acid; salicylic acid; p-hydroxybenzoic acid; β-resorcyclic acid; gallic acid; veratric acid; trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicylic acid; mandelic acid; levulinic acid; pyruvic acid; glycine; alanine; valine; isoleucine; leucine; phenylalanine; proline; serine; threonine; tyrosine; hydroxyproline; ornithine; lysine; arginine; histidine; hydroxylysine; phenylglycine; p-aminobenzoic acid; m-aminobenzoic acid; anthranilic acid; aspartic acid; glutamic acid; aminoadipic acid; glutamine; and asparagine.

For the purposes of this invention, the modified C-26 derivatives of bryostatin include those in which the antineoplastic activity of the compound is not eliminated, preferably is not significantly adversely affected, and more preferably not adversely affected at all, in comparison to the unmodified bryostatin, while the toxicity of the overall compound is diminished: Advantageously the toxicity is diminished at least ten-fold, more preferably diminished at least one-hundred-fold, even up to one-thousand fold, and most preferably diminished to the point of being unobservable in vivo under testing conditions commonly used in the art.

The C-26 position of the bryostatins is a chiral carbon center comprising a reactive secondary alcohol. It will be appreciated by one skilled in the art that the nature of this chiral center causes it to be well disposed to modification. In fact, several modifications at this position are already known in the art. For example, the production of the stereoisomer of bryostatin, 26-epibryostatin, is described in Petit et al. (*Anti-Cancer Drug Design,* 7, 101–113 (1992)) utilizing 26-oxobryostatin (which is also a C-26 modification of bryostatin 1) as a reactive intermediate. Additionally, the generation of C-26 alkyl esters of the bryostatins are also known in the art, for example, succinyl esters.

Suitable C-26 modifications for the purpose of the present invention are any that impair the accessibility of the hydroxymethyl group found at the C-26 position of bryostatin such that toxicity is diminished and antineoplastic activity is not eliminated. By way of example, such modifications include formation of a 26-epibryostatin, which is effective in reducing the toxicity of bryostatin by at least 10-fold. Further exemplary modifications comprise conversion of the hydroxyl-moiety to an oxo moiety, an oxime moiety, a methylenyl moiety, or an alkenyl or an alkynyl ester. Such modifications may further comprise, e.g., replacing the C-26 hydroxyl moiety with a moiety selected from the group consisting of hydrogen, a halide, cyanide, a $C_1$ to $C_6$ alkyl sulfonate, a aryl sulfonate, a $C_1$ to $C_6$ alkyl aryl sulfonate, a $C_1$ to $C_6$ alkyl carbonate, a $C_1$ to $C_6$ aldol, a $C_1$ to $C_6$ ketol, a $C_1$ to $C_6$ alkenyl, a methylenyl, a $C_1$ to $C_6$ alkyl urethane, a $C_1$ to $C_6$ alkyl ether, a $C_1$ to $C_6$ alkyl amine, a sulfate, a phosphate, a nitrate, an oxime, an amine, a semicarbazone, a thiosemicarbazone, and a $C_1$ to $C_6$ aminoalkane.

It should also be appreciated that the accessibility to the C-26 hydroxyl group also can be usefully diminished by the induction of steric hindrance near the C-26 position. By way of example, the methyl or hydrogen substituents of C-26 could be replaced by a tert-butyl moiety or similar bulky organic substituent containing up to 12 carbon atoms, preferably containing less than 9 carbon atoms, more preferably containing between 3 and 6 carbon atoms. The desirability of these substitutions should be measured by the ability to diminish toxicity of the unmodified bryostatin without eliminating the antineoplastic character of the unmodified bryostatin, thereby raising the therapeutic index of the derivative.

Thirteen macrocyclic lactone compounds of the bryostatin 1 family have been identified so far. Because *Bugula neritina* contains largely bryostatin 1, bryostatin 1 is currently the most abundantly available bryostatin. Therefore, bryostatin 1 has been the first member of this class of compounds to be tested in humans. However, in vitro experimental data obtained using five bryostatins (bryostatin 1, 2, 3, 4, and 10) indicate that all bryostatins cause similar effects, suggesting that all the bryostatins have potentially useful chemotherapeutic properties (Dell'Aquilla et al., supra (1988)).

Bryostatin 1 is currently in phase two clinical trials as an antineoplastic drug and has shown indications of utility in the treatment of cancer (see the Examples herein, as well as Philip et al., supra (1993); Lily et al., *Cancer Res.*, 50, 5520–5525 (1990); Drexler et al., *Blood*, 74, 1747–1757 (1989); Al-Katib et al., *Hematol. Oncol.*, 8, 81–89 (1990); Schuchter et al., *Cancer Res.*, 51, 682–687 (1991); Sredni et al., *Immunology*, 70, 473–477 (1990); Trenn et al., *J. Immunol.*, 140, 433–439 (1988)). In human trials, bryostatin 1 has been administered to patients suffering from, at least, ovarian adenocarcinoma, non-small-cell lung cancer, hypernephroma, maxillary carcinoma, carcinoid tumor, breast carcinoma, malignant melanoma, colorectal carcinoma, adenocarcinoma (e.g., those of unknown origin), esophageal carcinoma, small-cell lung cancer, and pancreatic carcinoma (Philip et al., supra (1993)). This set of cancers is limited more by the scale of clinical trials than by any perceived limits of cancer types that can be treated with bryostatin 1. Five cancerous conditions for which bryostatin 1 has been directly shown to be effective are lymphoma, renal cancer, melanoma, leukemia, and ovarian cancer. In view of the structural similarities between C-26 modified and unmodified bryostatins, and in view of the observed similarity in antineoplastic action between compounds, the range of suitable cancers treatable by C-26 modified bryostatins is expected to be at least as great as the range of cancers and other disease states treatable by bryostatin 1.

The C-26 modified bryostatins as described herein also will be of utility in veterinarian and human applications. In fact, the unmodified bryostatins (e.g., bryostatin 1) have been shown to be effective in in vitro growth assays (e.g., B16/F10 melanoma cells), and in both mice and humans. It is expected that C-26 modified bryostatins will have greater utility than unmodified bryostatins because the C-26 modified bryostatins are less toxic, at least ten-fold less toxic, to C57BL/6 mice. The similar ability of C-26 modified bryostatins to inhibit neoplastic growth, coupled with a significantly decreased toxicity, results in a relative therapeutic index which is significantly greater for the C-26 modified bryostatins than for the unmodified bryostatins.

The modified bryostatins useful in the context of the present inventive method can be administered to an animal, especially a mammal (e.g., a mouse), and preferably a human, by any suitable means or routes. Such administrative means or routes include, for example, orally, via inhalation, parenterally, topically, subcutaneously, intravenously, intramuscularly, intraperitoneally, rectally, and vaginally. Preferably the administrative means or route is chosen to maximize application of the modified bryostatin to the cancer cells while minimizing the exposure of non-cancerous cells to the therapeutic modified bryostatin. Of course, such optimized routes of administration can differ greatly between differing types of cancer.

The dose administered to an animal, particularly a human, in the context of the present invention should be sufficient to cause a desirable response, e.g., regression or remission of the cancerous state. One skilled in the art will recognize that dosage will depend upon a variety of factors including the strength of the particular modified bryostatin employed, the age, species, condition, and body weight of the animal, as well as the extent of the cancer. The size of the dose will also be determined by the route, timing, and frequency of administration as well as the existence, nature, and extent of any adverse side-effects that might accompany the administration of a particular modified bryostatin and the desired physiological effect.

The administration of C-26 modified bryostatins can be based upon the administration regimens developed for bryostatin 1, which is typically tolerated in humans at doses of less than 2 ug/kg. In view of this, the administration of the C-26 modified bryostatins can be optimized such that at least 10-fold higher dosages of drug compound can be administered. Preferably, the administration of quantities of C-26 modified bryostatins can exceed the quantities of bryostatin 1 by at least 100-fold, even up to 1000-fold. More preferably the administration of the modified bryostatin will be limited by diminution of the increase in antineoplastic effect relative to the increase of drug quantity, instead of by its toxicity. Of course, these values can be adjusted upward or downward by one skilled in the art to account for interindividual differences in susceptibility, responsiveness, and general health during the time of administration. In another embodiment of this invention, the quantity and timing of C-26 modified bryostatin administration is further modified by the parameters of administration. In yet another embodiment, suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. Of course, these dosages are expected to vary significantly depending on the overall therapeutic regime, particularly when C-26 modified bryostatins are administered in combination with other drugs or compounds which modulate the toxicity or effectiveness of the C-26 modified bryostatins.

The present invention also provides a pharmaceutical composition comprising a pharmaceutically acceptable carrier and a therapeutically effective amount of one or more of the C-26 modified bryostatins, useful in the context of the present inventive method. Any suitable carrier can be used in the pharmaceutical composition, which of course, will depend on the particular means or route of administration, as well as other practical considerations. Such practical considerations include, but need not be limited to, providing a carrier suitable for the relatively low aqueous solubility of bryostatins, a lack of reactivity with the modified bryostatins, and protection of the modified bryostatin from inactivation or degradation prior to delivery to target tissues.

The pharmaceutically acceptable carriers described herein, for example, vehicles, excipients, or diluents, are well-known to those who are skilled in the art and are readily available to the public. Accordingly, there is a wide variety of suitable formulations of the pharmaceutical composition of the present invention. The following formulations are merely exemplary and not meant to be limiting.

Injectable formulations are among those formulations that are preferred in accordance with the present inventive methods. The requirements for effective pharmaceutical carriers for injectable compositions are well known to those of ordinary skill in the art (See *Pharmaceutics and Pharmacy Practice,* J. B. Lippincott Company, Philadelphia, Pa., Banker and Chalmers, eds., pages 238–250, (1982); *ASHP Handbook on Injectable Drugs,* Toissel, 4th ed., pages 622–630 (1986)). It is preferred that such injectable compositions be administered intravenously or locally, i.e., at or near the site of the cancer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The modified bryostatin may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkylimidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations are well-known to those of skill in the art and are suitable in the context of the present invention. Such formulations are typically applied to skin or other body surfaces.

Formulations suitable for oral administration can consist of (a) liquid solutions, such as an effective amount of the C-26 modified bryostatin dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The C-26 modified bryostatins useful in the present inventive method, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the C-26 modified bryostatins useful in the present inventive method can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

In addition to the above described pharmaceutical compositions, the modified bryostatins of the present inventive method can be formulated as inclusion complexes, such as cyclodextrin inclusion complexes, or in liposomes.

The following examples further illustrate the present invention but, of course, should not be construed as in any way limiting its scope.

EXAMPLE 1

This example illustrates the antineoplastic activity of bryostatin 1 and a C-26 modified bryostatin, 26-epibryostatin 1.

The unmodified and C-26 modified bryostatins were used in [$^3$H]thymidine incorporation and cell proliferation assays. The phorbol ester PMA, a ligand for protein kinase C was also used in this example to provide a separate control sample. The selection of PMA as a control sample is particularly appealing since bryostatins antagonize a subset of the actions of PMA. [$^3$H]Thymidine incorporation is a measure of DNA synthesis, which is often used as a marker of cell replication. Chronic cell growth assays are an alternative measure of cell growth, usually performed over longer periods of time.

For the cell proliferation assays, the B16-F10 melanoma cell line with high pulmonary metastatic potency (from the laboratory of Dr. I. J. Fidler, Frederick Cancer Research and Development Center, Frederick, Md.) were plated at a density of $10^3$ cells/well in Costar 12-well tissue culture plates. The cells were then treated with different concentrations of bryostatin 1, 26-epi-bryostatin 1, or PMA in 0.1% DMSO 1 and 3 days after plating. Total cell number was determined 4 days after plating.

For [$^3$H]-thymidine incorporation assays, melanoma cells growing in log phase at a density of 40–50% confluency were treated for one day with the indicated compound.

Figure 2A:
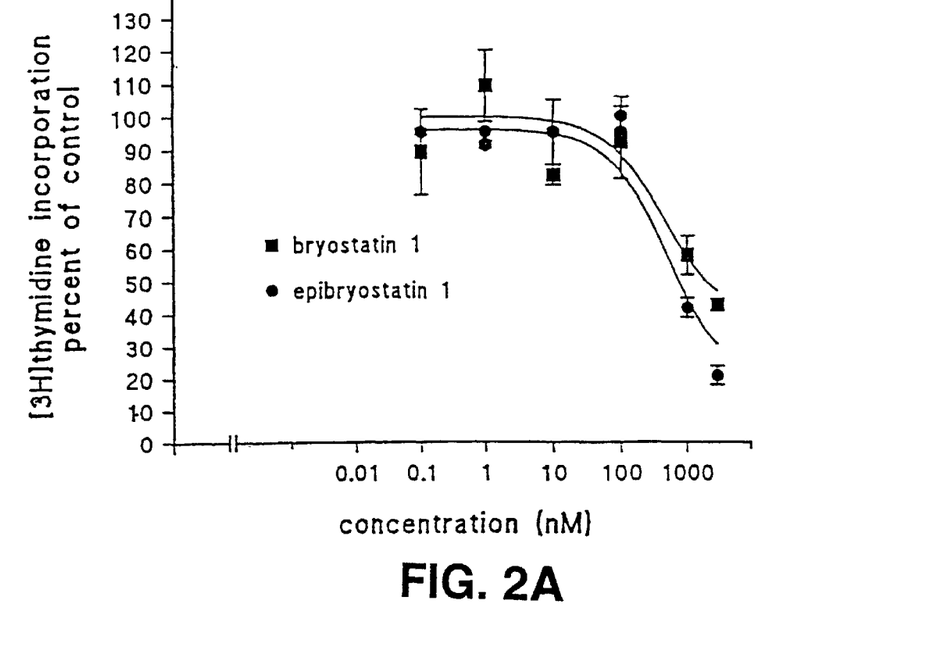
FIG. 2A depicts the percentage of incorporation of [$^3$H] thymidine relative to a control sample (y-axis) plotted as a function of the concentration (nM) of bryostatin 1 (squares) or 26-epibryostatin 1 (circles)
Figure 2B:
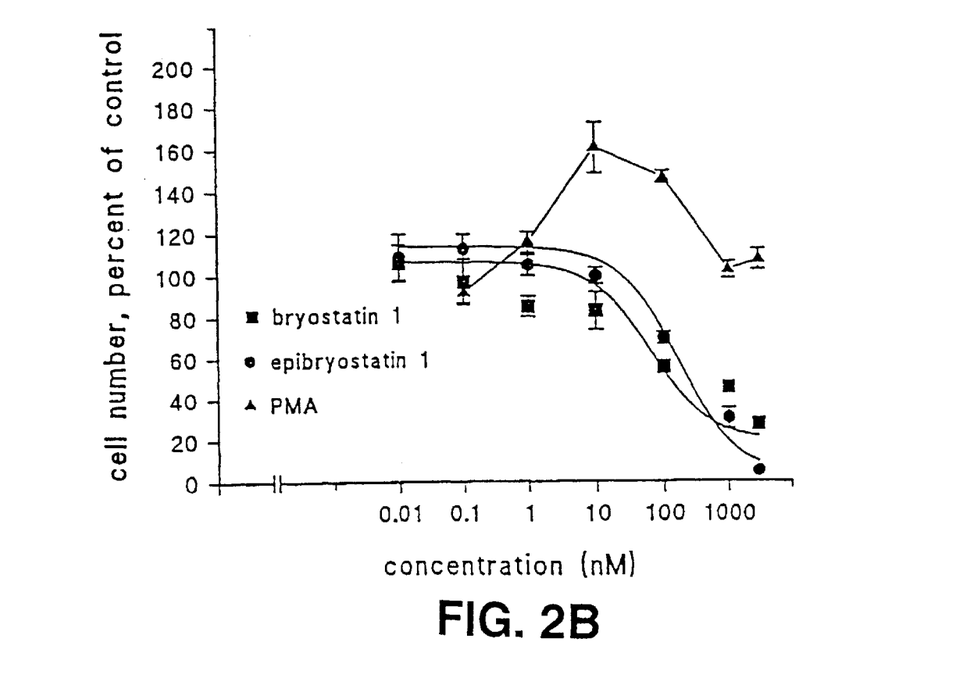
FIG. 2B depicts the results of a chronic cell growth assay wherein the number of cells expressed as a percentage of a control sample (y-axis) are plotted as a function of the concentration (nM) of bryostatin 1 (squares), 26-epibryostatin 1 (circles), or PMA (triangles).

The effect of bryostatin 1 and phorbol 12-myristate 13-acetate (PMA) on the proliferation of the B16/F10 melanoma cell line was first determined. Bryostatin 1 inhibited [$^3$H]thymidine incorporation with an $ED_{50}$ of 600±80 nM (n=3) and with a maximum inhibition of 60% (FIG. 2A). PMA showed no significant effect on the [$^3$H]thymidine incorporation tested over a dose range between 0.1 nM to 3 uM (data not shown) except for a slight increase (120±20%) at 10 nM PMA. The effect on cell growth of chronic treatment with bryostatin 1 or PMA was also determined. Bryostatin 1 showed 75±5% (n=3) inhibition of cell growth after 4 days of treatment at the highest dose tested (3 uM); the dose required to achieve an effective reduction in growth of 50% ($ED_{50}$) was 50±15 nM (n=3) (FIG. 2B). A trypan blue dye exclusion test, which measures cell viability, showed less than 1% cell death, indicating that bryostatin 1 arrested growth rather than killed cells. In contrast to bryostatin 1, PMA increased the cell growth by 75±10% (n=3) at a dose of 10 nM; the dose response curve was biphasic, with smaller effects at higher and lower applied doses (FIG. 2B).

Despite its significantly reduced affinity for protein kinase C, 26-epi-bryostatin 1 displayed inhibitory potency similar to that of bryostatin 1 in the [$^3$H]thymidine incorporation assay and showed only a 3-fold reduction in potency in the chronic cell growth assay (FIGS. 2A, 2B). Furthermore, the maximum extent of inhibition both of [$^3$H]thymidine incorporation and of cell growth was greater than for bryostatin 1 in both assays (FIG. 2A, 2B). In the [$^3$H]thymidine incorporation assay, the $ED_{50}$ of 26-epi-bryostatin 1 was 600±120 nM; the maximum inhibition of [$^3$H]thymidine incorporation was 80±5% at the highest dose tested (3 uM). In the chronic treatment schedule for cell growth, 26-epi-bryostatin 1 showed an $ED_{50}$ of 140±30 nM with a maximal inhibition of 97±3% at the highest dose tested (3 uM) (FIGS. 2A, 2B). During the 4-day treatment schedule, the number of cells in the control group increased 80 to 100-fold. These latter results show that 3 uM 26-epi-bryostatin 1 induced almost complete growth arrest. At the same time, a trypan blue exclusion test showed less than 1% cell death, evidencing that 26-epi-bryostatin 1, at this dose, is a powerful cytostatic agent with no cytotoxic effect.

EXAMPLE 2

This example illustrates a direct comparison of the toxicity of 26-epi-bryostatin 1 with that of bryostatin 1 in vivo.

C57BL/6 mice were injected with either 500 ug/kg or 1500 ug/kg 26-epi-bryostatin 1 or 150 ug/kg or 500 ug/kg bryostatin 1. The animals were observed for 7 days. The higher dose of bryostatin 1 was lethal for all animals tested by the third day after injection, whereas the lower dose of bryostatin 1 and both of the 26-epi-bryostatin 1 doses caused only relatively minor toxic effects. This example shows that 26-epi-bryostatin 1 is significantly less toxic than bryostatin 1 and indicates that 26-epi-bryostatin 1 has a higher therapeutic index relative to that of bryostatin 1.

EXAMPLE 3

This example demonstrates that the growth inhibition target of the bryostatins is not protein kinase C.

Bisindolyl-maleimide I was used to inhibit both PMA and bryostatin 1 induced protein kinase C activity and bryostatin 1 induced inhibition of [$^3$H]thymidine incorporation. Bisindolyl-maleimide I is a powerful and specific protein kinase C inhibitor (Toullec et al., *J. Biol. Chem.*, 266, 15771–15781 (1991)) and is therefore useful for determining the role of putative protein kinase C ligands in observable phenomena.

Protein kinase C activity was assayed in cell lysates by measuring the incorporation of $^{32}$P from [$\gamma$-$^{32}$P]ATP into acetylated myelin basic protein peptide (4-14) (Ac-MBP(4-14)) by methods known in the art (Nakadate et al., *Biochem. Pharmacol.*, 37, 1541–1545 (1988)). The cells were treated at 60–75% confluency with bryostatin 1, 26-epi-bryostatin 1 and/or bisindolyl-maleimide I for 10 min. The cells were lysed by sonication in 20 mM Tris-HCl, pH 7.4, containing 5 mM EGTA and 20 uM leupeptin. 5 ul of cell lysate was added to 15 ul kinase buffer (20 mM HEPES, pH 7.5, 10 mM $MgCl_2$, 0.5 mM $CaCl_2$, 1 mM 4-(2-aminoethyl) benzenesulfonyl fluoride, 20 uM leupeptin, and 10 ug/ml aprotinin) containing 50 uM substrate, and 2 uCi [$\gamma$-$^{32}$P]ATP at a concentration 50 uM ATP. The kinase reaction was incubated for 10 minutes at 30 ° C. The incorporated radioactivity was measured with a Pharmacia Biotech 1218 liquid scintillation counter. The resulting data is set forth in Table 2.

Table 2

The effect of bisindolyl-maleimide I cotreatment on induction of protein kinase C activity and [$^3$H]thymidine incorporation in response to PMA or bryostatin 1.

| Treatment | BIM-I (1 uM) | fold increase of protein kinase C activity | [³H] thymidine incorporation expressed as percent of control |
|---|---|---|---|
| PMA (10 nM) | + | 0.54 ± 0.03 | 91 ± 2 |
| | − | 4.4 ± 0.1 | 120 ± 22 |
| Bryostatin 1 (3 uM) | + | 1.08 ± 0.1 | 98 ± 11 |
| | − | 3.02 ± 0.3 | 43 ± 2 |
| Epi-bryostatin1 (3 uM) | + | 1.07 ± 0.04 | 25 ± 5 |
| | − | N.D. | 21 ± 3 |
| | + | N.D. | 20 ± 5 |

As is apparent from the data set forth in Table 2, bisindolyl-maleimide I completely inhibited PMA or bryostatin 1 induced protein kinase C enzymatic activity (Table 2). At the same doses tested, bisindolyl-maleimide I inhibited the modest PMA-induced increase in [³H]thymidine incorporation, consistent with protein kinase C mediating this modest growth stimulation. In contrast, bisindolyl-maleimide I did not block the inhibition of thymidine incorporation by bryostatin 1. Rather, it slightly enhanced the bryostatin induced decrease in [²H]thymidine incorporation. Interestingly, the combination of bryostatin 1 and bisindolyl-maleimide I indicated the same level of inhibition of [3H]thymidine incorporation as 26-epi-bryostatin 1 alone. The inhibitor results mitigate against a role for protein kinase C in the growth inhibition. Further, these surprising results support the concept that the toxicity of bryostatin is mediated through a protein kinase C dependent pathway while the antineoplastic activity is mediated through a separate pathway.

EXAMPLE 4

The bryostatin derivatives useful in the context of the present invention can be synthesized essentially according to the method of Pettit et al., *Anticancer Drug Design*, 7, 101–103 (1992). Illustrative of the method is the synthesis of 26-oxo-bryostatin 1. Briefly, a bryostatin is dissolved in anhydrous methylene chloride under nitrogen. Pyridinium dichromate (PDC; 5 equivalents) is added to the solution and stirred at 25° C. for about 24 hours. An additional 5 equivalents of PDC is then added and stirred for another 24 hours. After removing the solvent (e.g., in vacuo), the remaining orange brown material is taken up in ethyl acetate and filtered through Celite. The ethyl acetate is removed under pressure, and the remaining yellow tinted solid is isolated by silica gel column chromatography in a suitable solvent (e.g., 50% ethyl acetate, 50% hexane). While other routes of synthesis are possible, the illustrated method gives good yields of the 26-oxo-bryostatin approximating 90% of the theoretical yield.

EXAMPLE 5

26-epi-bryostatin also can be made according to the method of Pettit et al. (supra). 26-oxo-bryostatin obtained as in Example 4 is dissolved in anhydrous organic solvent (e.g., methanol) and reduced by addition of excess reducing agent (e.g., 25 equivalents of sodium borohydride). After stirring for about 1 hour, the reaction is quenched by addition of 1 N HCl or other suitable reagents. The solvent is then removed (e.g., under pressure). The product is then re-dissolved in a small amount of ethanol, followed by filtration through Celite or other suitable material and elution in methylene chloride. The produced 26-epi-bryostatin can be separated from the regenerated brysotatin (unmodified) via normal phase HPLC on a Phenomenex Prepex (5–20 m) column in 20:3:1 hexane:methylene chloride:isopropanol. The product can be detected by absorption at 254 nm.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of treating cancer in an animal comprising administering to an animal afflicted with cancer a therapeutically effective amount of a bryostatin which has been modified at the C-26 position, wherein said modification impairs the accessibility of the hydroxymethyl group found at the C-26 position of bryostatin such that the modified bryostatin lacks affinity for protein kinase C, antineoplastic activity is maintained and toxicity is diminished.

2. The method of claim 1, wherein the modified bryostatin is a 26-epi-bryostatin.

3. The method of claim 1, wherein the modified bryostatin is a 26-oxo-bryostatin.

4. The method of claim 2, wherein said bryostatin is a compound of the following formula and $R_1$ and $R_2$ are independently selected from the group consisting of hydrogen, hydroxyl, and an organic substituent having from 1 to 20 carbon atoms.

5. The method of claim 4, wherein $R_1$ and $R_2$ are independently selected form the group consisting of:

-continued

6. The method of claim 2, wherein the modified bryostatin is 26-epi-bryostatin 1, 26-epi-bryostatin 2, 26-epi-bryostatin 4, 26-epi-bryostatin 5, 26-epi-bryostatin 6, 26-epi-bryostatin 7, 26-epi-bryostatin 8, 26-epi-bryostatin 9, 26-epi-bryostatin 10, 26-epi-bryostatin 11, 26-epi-bryostatin 12, or 26-epi-bryostatin 13.

7. The method of claim 6, wherein the modified bryostatin is 26-epi-bryostatin 1.

8. The method of claim 3, wherein the modified bryostatin is 26-oxo-bryostatin 1, 26-oxo-bryostatin 2, 26-oxo-bryostatin 4, 26-oxo-bryostatin 5, 26-oxo-bryostatin 6, 26-oxo-bryostatin 7, 26-oxo-bryostatin 8, 26-oxo-bryostatin 9, 26-oxo-bryostatin 10, 26-oxo-bryostatin 11, 26-oxo-bryostatin 12, or 26-oxo-bryostatin 13.

9. The method of claim 8, wherein the modified bryostatin is 26-oxo-bryostatin 1.

10. The method of claim 1, wherein the animal is human.

11. The method of claim 1, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

12. The method of claim 11, wherein the cancer is selected from the group consisting of lymphoma, leukemia, melanoma, renal cancer, and ovarian cancer.

13. The method of claim 3, wherein said bryostatin is a compound of the following formula and $R_1$ and $R_2$ are independently selected from the group consisting of hydrogen, hydroxyl, and an organic substituent having from 1 to 20 carbon atoms.

14. The method of claim 13, wherein $R_1$ and $R_2$ are independently selected from the group consisting of:

15. The method of claim 2, wherein the animal is human.
16. The method of claim 3, wherein the animal is human.
17. The method of claim 4, wherein the animal is human.
18. The method of claim 5, wherein the animal is human.
19. The method of claim 6, wherein the animal is human.
20. The method of claim 7, wherein the animal is human.
21. The method of claim 8, wherein the animal is human.
22. The method of claim 9, wherein the animal is human.
23. The method of claim 2, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

24. The method of claim 3, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

25. The method of claim 4, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

26. The method of claim 5, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

27. The method of claim 6, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

28. The method of claim 7, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

29. The method of claim 8, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

30. The method of claim 9, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

31. The method of claim 10, wherein the cancer is selected from the group consisting of non-small-cell lung cancer, hypernephroma, maxillary carcinoma, carcinoid tumor, breast carcinoma, colorectal carcinoma, esophageal carcinoma, small-cell lung cancer, pancreatic cancer, lymphoma, leukemia, melanoma, renal cancer, ovarian cancer, and adenocarcinoma.

32. The method of claim 23, wherein the cancer is selected from the group consisting of lymphoma, leukemia, melanoma, renal cancer, and ovarian cancer.

33. The method of claim 24, wherein the cancer is selected from the group consisting of lymphoma, leukemia, melanoma, renal cancer, and ovarian cancer.

34. The method of claim 25, wherein the cancer is selected from the group consisting of lymphoma, leukemia, melanoma, renal cancer, and ovarian cancer.

35. The method of claim 26, wherein the cancer is selected from the group consisting of lymphoma, leukemia, melanoma, renal cancer, and ovarian cancer.

36. The method of claim 27, wherein the cancer is selected from the group consisting of lymphoma, leukemia, melanoma, renal cancer, and ovarian cancer.

37. The method of claim 28, wherein the cancer is selected from the group consisting of lymphoma, leukemia, melanoma, renal cancer, and ovarian cancer.

38. The method of claim 29, wherein the cancer is selected from the group consisting of lymphoma, leukemia, melanoma, renal cancer, and ovarian cancer.

39. The method of claim 30, wherein the cancer is selected from the group consisting of lymphoma, leukemia, melanoma, renal cancer, and ovarian cancer.

40. The method of claim 31, wherein the cancer is selected from the group consisting of lymphoma, leukemia, melanoma, renal cancer, and ovarian cancer.

* * * * *